United States Patent
Pender

[11] Patent Number: 5,944,711
[45] Date of Patent: Aug. 31, 1999

[54] EAR-IRRIGATING METHOD AND DEVICE

[76] Inventor: Daniel J. Pender, P.O. Box 1090, Long Beach, N.Y. 11561

[21] Appl. No.: 08/994,196

[22] Filed: Dec. 19, 1997

[51] Int. Cl.[6] ............................. A61M 31/00; A61F 9/00
[52] U.S. Cl. ............................................ 604/514; 606/162
[58] Field of Search ......................... 128/864; 606/109, 606/162; 607/137; 600/200, 563, 111, 112; D24/137, 108; 604/35, 36, 38, 39, 41, 49, 54, 73, 93, 104, 187, 257, 290, 291, 313, 346

[56] References Cited

U.S. PATENT DOCUMENTS

| | | |
|---|---|---|
| 989,839 | 4/1911 | Powler . |
| 2,039,546 | 5/1936 | McGerry . |
| 3,651,808 | 3/1972 | White .................................... 604/213 |
| 4,036,235 | 7/1977 | Hathaway ............................. 604/346 |
| 4,201,212 | 5/1980 | Bradley . |
| 4,206,754 | 6/1980 | Grossan .................................. 604/39 |
| 4,282,867 | 8/1981 | Du Toit ................................. 604/151 |
| 4,995,867 | 2/1991 | Zollinger ................................. 604/54 |
| 5,312,332 | 5/1994 | Bales et al. ............................. 604/49 |
| 5,364,343 | 11/1994 | Apolet et al. ........................... 604/43 |
| 5,395,357 | 3/1995 | Weigel .................................... 604/346 |
| 5,476,446 | 12/1995 | Arenburg ................................. 604/54 |
| 5,490,836 | 2/1996 | Desai ...................................... 601/35 |
| 5,662,605 | 9/1997 | Hurwitz .................................. 604/54 |
| 5,665,094 | 9/1997 | Goldenberg ........................... 606/109 |

Primary Examiner—Corrine McDermott
Assistant Examiner—Sharon Finkel
Attorney, Agent, or Firm—Myron Amer PC

[57] ABSTRACT

Irrigating a patient's ear using an otoscope tip fitted to be seated in the ear canal, similar to the placement of a finger therein to block out noise, through which tip there is a continuous circulation of flushing fluid, wherein the seated position of the tip maintains the patient splatter-free and obviates use of a waterproof apron or the like.

1 Claim, 1 Drawing Sheet

EAR-IRRIGATING METHOD AND DEVICE

FIELD OF THE INVENTION

The present invention generally relates to improvements for an ear irrigation procedure of the type using water to flush cerumen and like debris from a patient's ear canal, the improvements more particularly greatly facilitating this procedure as well as obviating a splattering or other inconvenience to the patient.

BACKGROUND OF THE INVENTION

Removal of ear cerumen is required from time to time and is achieved by syringing body temperature or warm water into the patient's ear canal, as described and illustrated in U.S. Pat. No. 4,201,212 for "Surgical Apparatus For Use In Syringing A Patient's Ear" issued to Margaret E. Bradley on May 6, 1980. In carrying out this procedure, in which a syringe is the water-delivering device of choice, there is an inherent complication. That is, the use of a syringe which has a limited volume and therefore a limited amount of flushing warm water has to be removed from time to time during the ear canal irrigation procedure. Each time that the syringe is removed there is, of course, the loss of any fluid-tight seal and this results in leaking of any exiting flow of the irrigating or flushing warm water, in turn requiring the use of a waterproof apron, and the like, the latter being exemplified by the "Splatter-Free Ear Irrigation Device" of U.S. Pat. No. 5,395,357 issued to Perry L. Weigel on Mar. 7, 1995.

The present invention contemplates eschewing the use of a syringe in carrying out the ear irrigation procedure, which contributes the attendant benefit of more effectively maintaining the patient splatter-free without using a waterproof apron, as is typically the practice, or using other like garments, as well as providing other noteworthy benefits.

SUMMARY OF THE INVENTION

Broadly, it is an object of the present invention to overcome the foregoing and other shortcomings of the prior art.

More particularly, it is an object of the present invention to perform the ear irrigation procedure under a fluid-tight seal which is readily applied, much like, by analogy, inserting a finger in the ear canal to muffle or render inaudible external noise which, of course, is not the object of the within inventive method, but achieves an intended object of providing a fluid-tight seal to prevent splattering of the patient, all as will be better understood as the description proceeds.

BRIEF DESCRIPTION OF THE DRAWING

The description of the invention which follows, together with the accompanying drawings should not be construed as limiting the invention to the example shown and described, because those skilled in the art to which this invention appertains will be able to devise other forms thereof within the ambit of the appended claims.

Preliminarily it is to be generally understood that the prior art use of a syringe which has a limited volume and therefore a limited amount of flushing warm water has to be removed from time to time during the ear canal irrigation procedure. Each time that the syringe is discharged into the ear canal, it does result in the leaking of irrigating or flushing warm water exiting from the syringe which, in turn, requires the use of a waterproof apron, and the like.

DESCRIPTION OF THE PREFERRED EMBODIMENT

Figure 1:
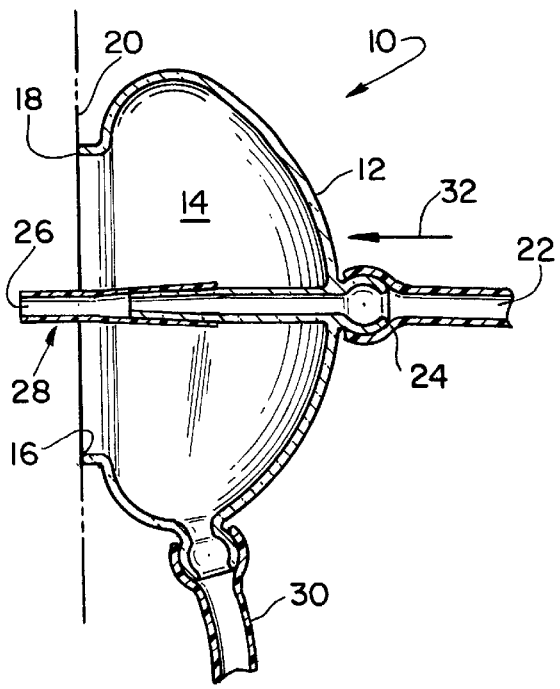
FIG. 1 is a side elevational view of a prior art device for flushing wax debris or so-called cerumen from an ear canal of a patient.

A solution addressing this problem is described and illustrated in U.S. Pat. No. 989,839 for "Ear Irrigating Device" issued to E. P. Fowler on Apr. 18, 1911, a representative pertinent drawing from this patent being identified as FIG. 1. The prior art device 10 includes a glass bulb-like ear-covering component 12 bounding an internal compartment 14 sized to fit over a patient's ear (not shown) having an opening 16 opening into the compartment 14 which is bounded by an edge 18 that during use of the device 10 is held against area 20 surrounding the patient's ear, in an effort to establish a fluid-tight seal at the site of engagement between the area 20 and the edge 18.

Beneath the glass ear cover 12 and thus under the observation of a qualified physician or the like, body temperature water is fed from a syringe (not shown) through a rear opening 22 of a nozzle 24 and through a front opening 26 of a tip 28 of the nozzle 24 into a patient's ear canal, and exits through a flexible tube 30 or the like with flushed-out cerumen. During repeated use of syringe-supplied flushing water, the fluid-tight seal at the engagement site of area 20 and edge 18 must be maintained to prevent splattering the patient. Even assuming an effort being made to exert an extent of pressure in the direction of arrow 32 contributing to maintaining the fluid-tight seal 18, 20 there is a tendency in the device of the '839 patent and in all known more modern devices to leak because of bony and raised and recessed areas in the surrounding head area 20 resulting in failure to establish total surface-to-surface contact between the head area 20 and the ear-cover front opening edge 18.

Figure 2:
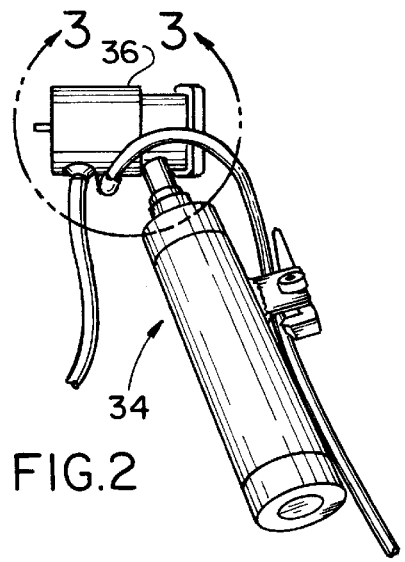
FIG. 2 is a perspective view of a so-called otoscope typically used for cerumen removal embodying the within inventive structural features and having the within inventive operating mode.

Underlying the present invention is the recognition that an operating mode which contemplates the use of a continuous warm water supply under pressure is one which obviates the removal of the ear-irrigating instrument prior to an observed completion of cerumen removal. This operating mode as just very generally described correspondingly obviates the need for the use of a waterproof apron as is made necessary by an instrument removal and the loss of seal between the ear speculum and the wall bounding the ear canal. That is, in the operating mode of the within inventive otoscope instrument, designated 34 in FIG. 2, the flushing warm water is removed by a vacuum pump to a sump and there is no release of the seal between the otoscope tip and the wall bounding the ear canal until the cerumen removal is completed, all as will now be explained in reference to FIGS. 2 and 3.

Figure 3:
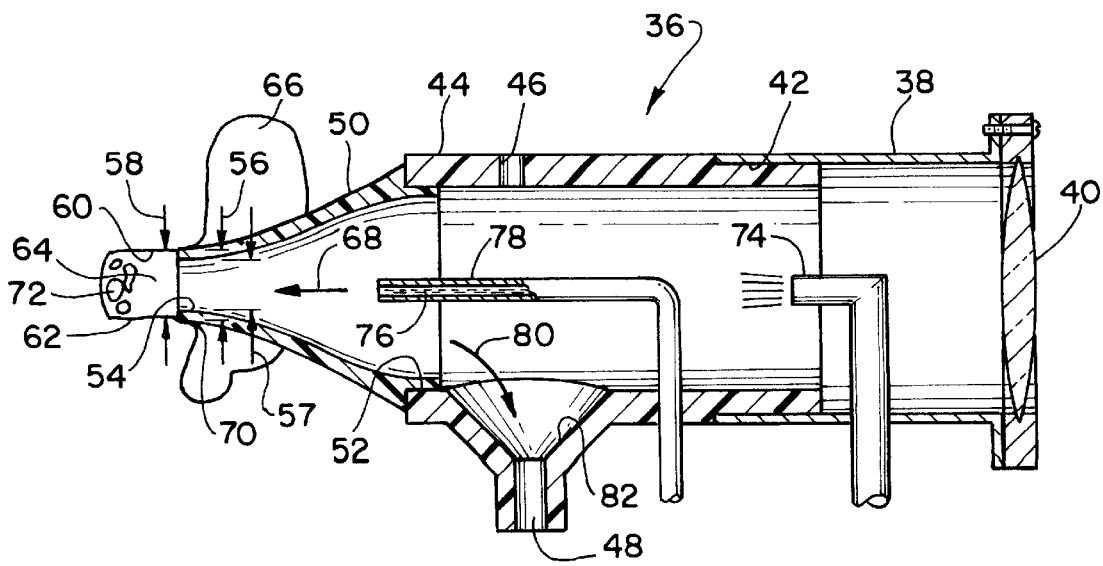
FIG. 3 is a partial sectional view, on an enlarged scale, of the ear canal-receiving tip of the otoscope.

The otoscope 34 has, pertinent to the within inventive operating mode, a flushing water delivery and removal head 36 shown in enlarged scale and in longitudinal cross section in FIG. 3. In a preferred embodiment of three cooperating housing components, head 36 has a rear cylindrical housing member 38 with a view port lens 40 telescoped, as at 42, to a medial housing member 44 with an air vent 46 diametrically opposite a flushing water exit port 48, and, as its third housing component, a front tip, generally designated 50, telescoped, as at 52, to extend forwardly of the medial housing member 44.

The front opening 54 of the inside diameter 57 bounds a tip 50 is of a cylindrical shape in cross section and of a selected outside diameter 56, wherein the selected diameter is slightly oversized with respect to a diameter 58 of an anatomical opening 60 bounded by the ear speculum or wall 62 bounding the ear canal 64 of the patient's ear 66. In use, the tip 50 is inserted in the direction 68 towards and into the ear canal 64 until established contact of the differing diameters 56 and 58 is made much like a friction fit, as at 70. This friction fit 70 is analogous to inserting a finger in the ear canal to muffle or render inaudible external noise which, of course, is not the object of the within inventive method, but achieves an intended object of providing a fluid-tight seal at the site 70.

Still referring to FIG. 3, it is noted for completeness' sake that visibility to observe the removal of cerumen 72 is provided by a fiber optic light source 74, that body temperature flushing water 76 is delivered under appropriate pressure from a pump through a nozzle 78 in a direction towards the ear canal 64 from whence it returns with cerumen 72 in an opposite direction 80 into a conical well shape 82 having the noted exit port 48 to a sump in which the exiting water, that is laden with cerumen 72, is appropriately disposed of at the option of the physician, it being important only that the fluid-tight seal or friction fit seal is maintained during the flowing in, and the exiting flow from, the ear until observation through the lens 40 indicates that the removal of cerumen 72 is completed.

While the apparatus for practicing the within inventive method, as well as said method herein shown and disclosed in detail is fully capable of attaining the objects and providing the advantages hereinbefore stated, it is to be understood that it is merely illustrative of the presently preferred embodiment of the invention and that no limitations are intended to the detail of construction or design herein shown other than as defined in the appended claims.

What is claimed is:

1. A method of irrigating a patent's ear using an otoscope of a type having an operating mode of flushing cerumen therefrom with body temperature water, said method comprising the steps of configuring a tip of said otoscope in a cylindrical shape in cross section and of a selected outside diameter, selecting a tip outside diameter that is slightly oversized with respect to a diameter of an anatomical opening of said patient's ear canal, inserting said tip into said ear canal, establishing at a site of engagement of said different diameters of said tip and said ear canal opening a friction fit obviating fluid leakage externally of said site, providing a source of body temperature water and a return sump therefore, and continuously flowing said body temperature water from said source into and removing water and cerumen from said ear of said patient for return to said sump through said tip until the removal of cerumen is completed, whereby a maintained said fluid leakage seal during said continuous flowing of said body temperature water obviates a splattering of said patient.

* * * * *